United States Patent [19]

Ife

[11] Patent Number: 4,652,650
[45] Date of Patent: Mar. 24, 1987

[54] PYRIDYLAMINOALKYLAMINE INTERMEDIATES

[75] Inventor: Robert J. Ife, Stevenage, England

[73] Assignee: Smith Kline & French Laboratories Limited, Welwyn Garden City, England

[21] Appl. No.: 762,486

[22] Filed: Aug. 5, 1985

Related U.S. Application Data

[62] Division of Ser. No. 563,497, Dec. 20, 1983, Pat. No. 4,548,940.

[30] Foreign Application Priority Data

Dec. 23, 1982 [GB] United Kingdom ............... 8236636

[51] Int. Cl.$^4$ .......................................... C07D 213/38
[52] U.S. Cl. .................................. 546/289; 546/297; 546/304; 546/307
[58] Field of Search ............... 546/286, 304, 297, 296, 546/289, 311, 307

[56] References Cited

U.S. PATENT DOCUMENTS

| | | | |
|---|---|---|---|
| 3,535,328 | 10/1970 | Zielinski | 546/275 |
| 3,553,292 | 1/1971 | Stahly et al. | 525/26 |
| 4,154,834 | 5/1979 | Brown et al. | 514/272 |
| 4,218,452 | 8/1980 | Brown et al. | 514/272 |
| 4,405,790 | 9/1983 | McGill et al. | 546/304 |
| 4,532,246 | 7/1985 | Ife | 514/275 |
| 4,547,506 | 10/1985 | Ife | 514/272 |

OTHER PUBLICATIONS

Whitmore et al., Journal of the American Chemical Society, vol. 67, No. 5, pp. 393–395, Mar. 1945.
Batzri et al., Chem. Abst. vol. 100:29483d (1984).
Bertaccini et al., Chem. Abst. vol. 100:61607h (1984).
Kaldrikyan et al., Chem. Abst. 78:124533f (1973).
Teikoku Hormone Mfg. Co. Ltd., Chem. Abst. 100:191885h (1984).
Kitteringham et al., Chem. Abst. 101:7191a (1984).
Burger, Med. Chem. 2nd Ed., p. 42 (1960).

Primary Examiner—Alan L. Rotman
Attorney, Agent, or Firm—Linda E. Hall; Stuart R. Suter; Alan D. Lourie

[57] ABSTRACT

Pyridine derivatives are disclosed which are useful as histamine $H_1$-antagonists.

2 Claims, No Drawings

PYRIDYLAMINOALKYLAMINE INTERMEDIATES

This is a division of application Ser. No. 563,497 filed Dec. 20, 1983, now U.S. Pat. No. 4,548,940, issued Oct. 22, 1985.

This invention relates to certain pyrimidone derivatives, a process for their preparation, compositions containing them and their use as histamine $H_1$-antagonists.

Histamine, a physiologically active compound endogenous in mammals, exerts its action by interacting with certain sites called receptors. One type of receptor is known as a histamine $H_1$-receptor (Ash and Schild, Brit. J. Pharmac. 1966, 27, 427) and the actions of histamine at these receptors are inhibited by drugs commonly called "antihistamines" (histamine $H_1$-antagonists) a common example of which is mepyramine.

A class of pyrimidone derivatives has now been discovered the members of which have histamine $H_1$-antagonist activity and are useful for the treatment of diseases (for example bronchial asthma, rhinitis, hayfever and allergic eczema) whose symptoms are mediated through the action of histamine at $H_1$-receptors.

Accordingly, the present invention provides compounds of formula (1):

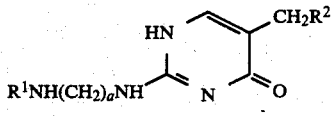

and pharmaceutically acceptable acid addition salts thererof where $R^1$ is 2- or 3-pyridyl optionally bearing one or two substituents which are the same or different and which are $C_{1-4}$ alkyl, $C_{1-4}$ alkoxy, halogen, nitro, cyano or trifluoromethyl;

a is 2 to 4; and $R^2$ is phenyl optionally bearing one or two substituents which are the same or different and are halogen, hydroxy, $C_{1-4}$ alkyl or $C_{1-4}$ alkoxy or a methylenedioxy group or is 3-pyridyl; N-oxo-3-pyridyl; 6-methyl-3-pyridyl; N-oxo-6-methyl-3-pyridyl; 6-hydroxymethyl-3-pyridyl; 4,6-dimethyl-3-pyridyl; N-oxo-4,6-dimethyl-3-pyridyl; 6-hydroxymethyl-4-methyl-3-pyridyl; 5,6-dimethyl-3-pyridyl; N-oxo-5,6-dimethyl-3-pyridyl; 6-hydroxymethyl-5-methyl-3-pyridyl; 4-pyridyl or N-oxo-4-pyridyl.

Examples of $C_{1-4}$ alkyl substituents for $R^1$ are methyl, ethyl and n-propyl.

Examples of $C_{1-4}$ alkoxy substituents for $R^1$ are methoxy, ethoxy and n-propoxy.

Examples of halogen substituents for $R^1$ are fluoro, chloro and bromo.

Preferably $R^1$ is an optionally substituted 2-pyridyl group.

Preferably the 2-pyridyl group $R^1$ has two substituents one of which is in the 3-position and one of which is in the 5-position.

Preferably the substituent in the 5-position is halogen and in particular it is chlorine.

Preferably the substituent in the 3-position is halogen or $C_{1-4}$ alkyl. More preferably it is $C_{1-4}$ alkyl and in particular it is methyl.

The value for a can be 2, 3, or 4. Thus —$(CH_2)_a$— can be ethane-1,2-diyl, propane-1,3-diyl or butane-1,4-diyl. Preferably a is 3 so that —$(CH_2)_a$— is propane-1,3-diyl. When $R^2$ is optionally substituted phenyl, preferably the phenyl group is substituted in the meta and/or para position relative to its point of attachment to the $CH_2$ group. Thus particular groups which $R^2$ represents are 3-methoxyphenyl, 4-bromophenyl, 4-chlorophenyl, 4-fluorophenyl, 4-hydroxyphenyl, 4-methoxyphenyl or 5-(3,4-methylenedioxyphenyl).

Preferably $R^2$ is 6-methyl-3-pyridyl.

The compounds of formula (1) are shown and described as 4-pyrimidones which exist in equilibrium with the corresponding 6-one tautomers. These compounds also exist to a lesser extent as the hydroxy tautomers, and the pyrimidine ring may also exist in the following tautomeric forms:

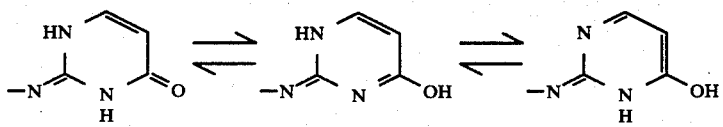

It will be understood that all these tautomeric forms are within the scope of the present invention.

The compounds of formula (1) form pharmaceutically acceptable salts with pharmaceutically acceptable salt-forming acids. Examples of these acids are hydrochloric, sulphuric, hydrobromic, phosphoric, tartaric, citric, maleic, lactic, 2-hydroxyethanesulphonic, methanesulphonic, toluene-4-sulphonic, ethanedisulphonic, ethanesulphonic and camphorsulphonic acids.

Compounds of formula (1) can be prepared by reacting a compound of formula (2):

where $R^1$ is as defined with reference to formula (1) and $X^1$ is halogen or a group —$NH(CH_2)_aNH_2$ where a is as defined with reference to formula (1) with a compound of formula (3):

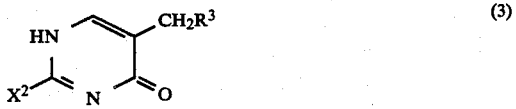

where $R^3$ is phenyl optionally bearing one or two substituents which are the same or different and are halogen, optionally protected hydroxy, $C_{1-4}$ alkyl or $C_{1-4}$ alkoxy or a methylenedioxy group or is 3-pyridyl; N-oxo-3-pyridyl; 6-methyl-3-pyridyl; N-oxo-6-methyl-3-pyridyl; 4,6-dimethyl-3-pyridyl; N-oxo-4,6-dimethyl-3-pyridyl; methyl-4-methyl-3-pyridyl; 5,6-dimethyl-3-pyridyl; N-oxo-5,6-dimethyl-3-pyridyl; 4-pyridyl or N-oxo-4-pyridyl;

$X^2$ is a group $NH_2(CH_2)_aNH$— where a is as defined with reference to formula (1) when $X^1$ is halogen, or is a group displaceable by amino when $X^1$ is a group —$NH(CH_2)_aNH_2$, thereafter removing any hydroxy protecting groups, optionally converting the compound of formula (1) so obtained where $R^2$ is N-oxo-6-methyl-3-pyridyl; N-oxo-4,6-dimethyl-3-pyridyl; N-oxo-5,6-dimethyl-3-pyridyl; into the corresponding compound of formula (1) where $R^2$ is 6-hydroxymethyl-3-pyridyl; 6-hydroxymethyl-4-methyl-3-pyridyl; or 6-hydroxymethyl-5-methyl-3-pyridyl; and thereafter optionally converting a compound of formula (1) so obtained into a salt.

The reaction can be carried out at an elevated temperature in the absence of a solvent, for example at from 80° C. to 170° C., preferably from 120° C. to 140° C., or in a solvent at an elevated temperature, for example at the reflux temperature of the reaction mixture. The choice of solvent is affected by solubility characteristics of the reactants. Preferably the solvent is pyridine, a picoline or mixture of picolines, a $C_{1-4}$ alkanol, preferably ethanol or 1-propanol, 1,2-ethanediol, a high boiling alkoxyaryl ether for example anisole, or a polar aprotic solvent, for example dimethylformamide, dimethylacetamide, dimethylsulphoxide, hexamethylphosphoramide, or sulpholane, Examples of groups $X^2$ are $C_{1-4}$ alkylthio (particularly methylthio), benzylthio, chlorine, bromine and nitroamino. Preferably $X^2$ is nitroamino.

The compounds of formula (1) where $R^2$ is N-oxo-6-methyl-3-pyridyl; N-oxo-4,6-dimethyl-3-pyridyl; or N-oxo-5,6-dimethyl-3-pyridyl can be converted into the corresponding compound of formula (1) where $R^2$ is 6-hydroxymethyl-3-pyridyl; 6-hydroxymethyl-4-methyl-3-pyridyl; or 6-hydroxymethyl-5-methyl-3-pyridyl; by reacting with an organic anhydride for example trifluoroacetic anhydride.

Examples of hydroxy protecting groups are methoxymethyl, methylthiomethyl, tetrahydropyranyl, arylmethyl, for example benzyl, $C_{1-6}$ alkyl, for example methyl, and alkanoyl, for example formyl or acetyl.

These protecting groups can be removed by standard methods, for example where the protecting group is alkanoyl or $C_{1-6}$ alkyl, by acid hydrolysis.

Pharmaceutically acceptable salts of compounds of formula (1) can be prepared by standard methods, for example by reacting a solution of the compound of formula (1) with a solution of the acid.

Compounds of formula (2) where $X^1$ is $-NH(CH_2)_aNH_2$ can be prepared by reacting a compound of formula (2) where $X^1$ is halogen with a diamine of formula (4):

$$NH_2(CH_2)_aNH_2 \qquad (4)$$

where a is as defined in formula (1).

Compounds of formula (3) where $X^2$ is $NH_2(CH_2)_aNH-$ can be prepared by reacting a compound of formula (3) where $X^2$ is a group displaceable with amine with a diamine of formula (4) as defined above.

These reactions, that is for the preparation of compounds of formula (2) where $X^1$ is $-NH(CH_2)_aNH_2$ and compounds of formula (3) where $X^2$ is $NH_2(CH_2)_aNH-$, can be carried out under conditions described above for the preparation of compounds of formula (1) that is at an elevated temperature in the absence of a solvent, for example at from 80° C. to 170° C., preferably from 120° C. to 140° C., or in a solvent at an elevated temperature, for example at the reflux temperature of the reaction mixture. The choice of solvent is affected by solubility characteristics of the reactants. Preferably the solvent is pyridine, a picoline or mixture of picolines, a $C_{1-4}$ alkanol, preferably ethanol or 1-propanol, 1,2-ethanediol, a high boiling alkoxyaryl ether for example anisole, or a polar aprotic solvent, for example dimethylformamide, dimethylacetamide, dimethylsulphoxide, hexamethylphosphoramide, or sulpholane.

Compounds of formula (2) where $X^1$ is halogen and compounds of formula (4) are known or can be made by analogy with known methods. Compounds of formula (3) where $X^2$ is a group displacable with amino are known or can be made by analogy with known methods as described in U.S. Pat. No. 4,145,546 and European Patent Application No. 0068833.

The histamine $H_1$-antagonist activity of the compounds of formula (1) can be demonstrated in vitro in the guinea pig ileum test. In this test an isolated portion of the guinea pig ileum is secured under tension (500 mg) between an anchorage and a transducer in a 10 ml tissue bath and immersed in magnesium free Tyrode solution with constant aeration at a temperature of 30° C. The output from the transducer is amplified. The amplified output is in turn fed to a flat bed recorder. Measured amounts of histamine are added to the tissue bath so that the histamine concentration increases stepwise until the force of the contraction reaches a maximum. The tissue bath is washed out and filled with fresh magnesium free Tyrode solution containing compound under test. The solution is left in contact with the tissue for 8 min. and measured amounts of histamine are added again until a maximum contraction is recorded. The assay is repeated with increasing concentrations of test compound and the dose of histamine giving 50% of maximum contraction is noted. A dose ratio (DR) was calculated by comparing the concentrations of histamine required to produce 50% maximum response in the absence and in the presence of the antagonist. A plot of Log DR-1 against Log D (the concentration of compound under test) is made and the point of intersection with the Log (DR-1) ordinate is taken as the measure of the activity ($pA_2$ value). The compounds of Examples 1 to 28 have $pA_2$ values greater than 6.

The activity of compounds of formula (1) as histamine $H_1$-antagonists can be demonstrated in vivo by the inhibition of histamine induced bronchoconstriction. Guinea pigs of either sex are anaesthetised by intraperitoneal injection of sodium pentobarbitone, 90 mg/kg. The trachea is cannulated. The animal is respired artificially with a fixed volume of air just adequate to inflate the lungs. The pressure needed to inflate the lungs is monitored from the respiratory system using a low pressure transducer. Intravenous injection of histamine causes dose-dependent increases in the pressure to inflate the lungs reflecting the bronchoconstrictor action of histamine. Responses to histamine can be antagonised using histamine $H_1$-receptor antagonists.

Dose-response curves to histamine are established at 20, 40, 80, 160 and 320 nmols/kg. Antagonists are then administered by intravenous injection and 5 minutes later a new histamine dose-response curve is established increasing the doses of histamine as necessary. The effect of the antagonist can be quantified by the displacement, to the right, of the histamine dose-response curve, expressed as a dose-ratio. A series of doses of antagonists may be given to each animal allowing calculation of dose-ratios for each dose of antagonist. The compounds of the Examples hereafter cause displacement of histamine dose-response curves with a dose-ratio of 10 at doses of less than 100 micromole kg$^{-1}$ i.v.

In order to use the compounds of the invention as histamine H$_1$-antagonists, they can be formulated as pharmaceutical compositions in accordance with standard pharmaceutical procedure.

The invention also includes pharmaceutical compositions comprising a compound of formula (1) or a pharmaceutically acceptable salt thereof and a pharmaceutically acceptable carrier.

Compounds of formula (1) and their pharmaceutically acceptable salts can be administered topically or systemically.

Topical formulations for administration to the skin include lotions and creams. Topical formulations for administration to the respiratory tract include solutions for application via a nebulizer or as an aerosol, or a microfine insufflatable powder. The active ingredient in an insufflatable powder has a small particle size i.e. less than 50 microns and preferably less than 10 microns. The active material is co-presented with a solid carrier for example lactose which has a particle size of less than 50 microns.

Systemic administration can be achieved by rectal, oral or parenteral administration. A typical suppository formulation comprises the active compound with a binding agent and/or lubricating agent for example gelatine or cocoa butter or other low melting vegetable waxes or fats. Typical parenteral compositions consist of a solution or suspension of the active material in a sterile aqueous carrier of parenterally acceptable oil.

Compounds of formula (1) which are active when given orally can be formulated as syrups, tablets, capsules and lozenges. A syrup formulation generally consists of a suspension or solution of the compound in a liquid carrier for example ethanol, glycerine or water with a flavouring or colouring agent. Where the composition is in the form of a capsule, the solid in granular form optionally with a binding agent is encased in a gelatin shell. Where the composition is in the form of a tablet, any suitable pharmaceutical carrier routinely used for preparing solid formulations can be used. Examples of such carriers include magnesium stearate, starch, lactose, glucose, sucrose, and cellulose. Preferably the composition is in unit dose form for example a tablet, capsule or metered aerosol.

Where appropriate, bronchodilators and anti-asthmatics for example sympathomimetic amines particularly isoprenaline, isoetharine, salbutamol, phenylephrine and ephedrine; xanthine derivatives particularly theophylline and aminophylline; and corticosteroids particularly prednisolone and adrenal stimulants particularly ACTH can be included.

Each dosage unit for oral administration contains preferably from 1 to 200 mg of a compound of formula (1) or a pharmaceutically acceptable salt thereof calculated as the free base.

The invention also provides a method of blocking histamine H$_1$-receptors which comprises administering to a subject an effective amount to block said receptors of a compound of formula (1) or a pharmaceutically acceptable salt thereof.

The compounds of formula (1) and their pharmaceutically acceptable salts will normally be administered to a subject in a pharmaceutical composition as described above, for the treatment of rhinitis, hayfever, bronchial asthma or allergic eczema. An adult subject will receive an oral dose of between 15 mg and 400 mg and preferably between 15 mg and 200 mg or an intravenous, subcutaneous or intramuscular dose of between 1 mg and 50 mg, and preferably between 1 mg and 10 mg of a compound of formula (1) or a pharmaceutically acceptable salt thereof calculated as the free base, the composition being administered 1 to 4 times per day.

The following Examples illustrate the invention.

EXAMPLE 1

(i) 2-Bromopyridine (20 g), 1,3-diaminopropane (47 g) and pyridine (13 ml) were heated together under reflux for 2.5 hr. The mixture was stripped to remove the excess of diaminopropane and the residue taken up in water. The pH was adjusted to 14 and extracted with chloroform. The extracts were dried (K$_2$CO$_3$), stripped and the residue distilled at reduced pressure to give 2-(3-aminopropylamino)pyridine (13.3 g; 70%) b.p.$_{0.02}$ 90°–91° C.

(ii) 2-(3-Aminopropylamino)pyridine (1.74 g) and 2-nitroamino-5-(6-methylpyrid-3-ylmethyl)-4-pyrimidone (2.0 g) were heated together under reflux in pyridine (8 ml) for 22 hr. The mixture was stripped, the residue triturated with ether and then water (the pH of which was adjusted to 6.5 with dilute acetic acid) to give a white solid. Recrystallisation from isopropanol gave 2-[3-(pyrid-2-ylamino)propylamino]-5-(6-methyl-pyrid-3-ylmethyl)-4-pyrimidone, (1.87 g; 70%), m.p. 163°–165° C.

C$_{19}$H$_{22}$N$_6$O+1.6% w/w isopropanol: Found: C, 64.84; H, 6.51; N, 23.41; requires: C, 65.04; H, 6.44; N, 23.60%.

EXAMPLE 2

(i) 2-Bromo-5-methylpyridine (17.2 g), 1,3-diaminopropane (37 g) and pyridine (10 ml) were heated together under reflux for 6 hr. The mixture was stripped to remove excess diaminopropane and the residue taken up in water. The pH was adjusted to 7.5 with conc. hydrochloric acid and extracted with chloroform. The aqueous solution was basified with conc. sodium hydroxide to pH 14 and extracted again with chloroform. The extracts were dried (K$_2$CO$_3$) and stripped to give 2-(3-aminopropylamino)-5-methylpyridine as an oil (9.95 g; 60%) which was used without further purification.

(ii) Substituting 2-(3-aminopropylamino)-5-methylpyridine (1.9 g) for 2-(3-aminopropylamino)pyridine and using the corresponding molar proportions of the other reagents in the method of Example 1(ii) gave 2-[3-(5-methylpyrid-2-ylamino)propylamino]-5-(6-methylpyrid-3-ylmethyl)-4-pyrimidone 2.2 H$_2$O, (1.54 g; 50%) m.p. 164°–166° C. on recrystallisation from isopropanol/water.

C$_{20}$H$_{24}$N$_6$O.2.2H$_2$O: Found: C, 59.49; H, 6.72; N, 20.84; requires: C, 59.45; H, 7.08; N, 20.80%.

EXAMPLE 3

(i) Substituting 2,5-dichloropyridino (5.00 g) for 2-bromo-5-methylpyridine and using the corresponding molar proportions of the other reagents in the method of Example 2(i) gave 2-(3-aminopropylamino)-5-chloropyridine as an oil (1.36 g) which was used without further purification.

(ii) Substituting 2-(3-aminopropylamino)-5-chloropyridine (1.3 g) for 2-(3-aminopropylamino)pyridine and using the corresponding molar proportions of the other reagents in the method of Example 1(ii) gave 2-[3-(5-chloropyrid-2-ylamino)propylamino]-5-(6-methylpyrid-3-ylmethyl)-4-pyrimidon 1.9 H$_2$O, (1.42 g; 58%) m.p. 173°–175° C. on recrystallisation from isopropanol/water.

C$_{19}$H$_{21}$ClN$_6$O.1.9H$_2$O: Found: C, 54.58; H, 5.70; N, 19.96; Cl, 8.66; requires: C, 54.45; H, 5.96; N, 20.05; Cl, 8.46%.

EXAMPLE 4

(i) Substituting 2,5-dibromopyridine (10 g) for 2-bromo-5-methylpyridine and using the corresponding molar proportions of the other reagents in the method of Example 2(i) gave 2-(3-aminopropylamino)-5-bromopyridine as an oil (9.1 g) which was used without further purification.

(ii) Substituting 2-(3-aminopropylamino)-5-bromopyridine (0.69 g) for 2-(3-aminopropylamino)pyridine and using the corresponding molar proportions of the other reagents in the method of Example 1(ii) gave, after chromatography (silica gel, 5% ammoniacal methanol/dichloromethane), 2-[3-(5-bromopyrid-2-ylamino)propylamino]-5-(6-methylpyrid-3-ylmethyl)-4-pyrimidone monohydrate, (0.31 g; 28%) m.p. 186°–187° C. on recrystallisation from isopropanol/water.

C$_{19}$H$_{21}$BrN$_6$O.1H$_2$O: Found: C, 51.22; H, 5.13; N, 18.72; Br, 17.59; requires: C, 51.01; H, 5.18; N, 18.79; Br, 17.86%.

EXAMPLE 5

(i) 2-Chloro-5-trichloromethylpyridine (5.0 g) and antimony trifluoride (3.88 g) were heated together on an oil bath at 170° C. to form a homogeneous oil. Heating was continued under reflux for a further 5 minutes after which time the condenser was directed downwards and the distillate (b.p. 135°–140° C.) collected. The distillate was taken up in dichloromethane and washed successively with 10% hydrochloric acid and water. After drying (MgSO$_4$), the solution was stripped to give an oil (1.84 g) which was found to be a mixture of 2-chloro-5-trifluoromethylpyridine and 2-fluoro-5-trifluoromethylpyridine by GLC/mass spec (ratio ca. 3:1).

(ii) The mixture from the method of Example 5(i) (1.8 g) in pyridine(1 ml) was added dropwise to 1,3-diaminopropane (4.1 ml) with stirring at room temperature. After 24 hr. the mixture was stripped, the residue taken up in water and the pH adjusted to 6.0 with hydrochloric acid. The solution was extracted with chloroform and the pH adjusted to 12.5 with sodium hydroxide. Extraction with ether gave, after drying (K$_2$CO$_3$) and stripping, 2-(3-aminopropylamino)-5-trifluoromethylpyridine as an oil (0.86 g) which was used without further purification.

(iii) Substituting 2-(3-aminopropylamino)-5-trifluoromethyl pyridine (0.80 g) for 2-(3-aminopropylamino)pyridine and using the corresponding molar proportions of the other reagents in the method of Example 1(ii) gave 2-[3-(5-trifluoromethylpyrid-2-ylamino)propylamino]-5-(6-methylpyrid-3-ylmethyl)-4-pyrimidone dihydrate, (0.96 g; 75%) m.p. 220°–223° C. on recrystallisation from isopropanol/water.

C$_{20}$H$_{21}$F$_3$N$_6$O.2H$_2$O: Found: C, 52.52; H, 5.08; N, 18.22; requires: C, 52.82; H, 5.55; N, 18.48%.

EXAMPLE 6

(i) 1,3-Diaminopropane (60 ml) and 2-nitroamino-5-(6-methylpyrid-3-ylmethyl)-4-pyrimidone (5.22 g) were heated together under reflux for 2.5 hr. Excess amine was stripped off and the residue recrystallised from ethanol to give 2-(3-aminopropylamino)-5-(6-methylpyrid-3-ylmethyl)-4-pyrimidone, (4.3 g; 79%) m.p. 162°–164° C.

(ii) 2-Chloro-5-cyanopyridine (0.61 g), 2-(3-aminopropylamino)-5-(6-methylpyrid-3-ylmethyl)-4-pyrimidone (1.09) and potassium carbonate (0.61 g) were heated together under reflux in pyridine (10 ml) for 2.5 hr. The mixture was stripped, the residue taken up in water and the pH adjusted to 3 with hydrochloric acid. After extracting with chloroform the aqueous solution was filtered and the pH raised to 6.5 with sodium hydroxide. The precipitate thus obtained was chromatographed (silica gel, chloroform/methanol, graded 1:0 to 20:1) and the required component recrystallised twice from ethanol to give 2-[3-(5-cyanopyrid-2-ylamino)propylamino]-5-(6-methylpyrid-3-ylmethyl)-4-pyrimidone 0.2 H$_2$O, (0.38 g; 25%) m.p. 175°–177° C.

C$_{20}$H$_{21}$N$_7$O.0.2H$_2$O: Found: C, 63.40; H, 5.79; N, 25.95; requires: C, 63.37; H, 5.69; N, 25.87%.

EXAMPLE 7

(i) Substituting 2-bromo-3-methylpyridine (10 g) for 2-bromo-5-methylpyridine and using the corresponding molar proportions of the other reagents in the method of Example 2(i) gave 2-(3-aminopropylamino)-3-methylpyridine (6.93 g) as an oil which was used without further purification.

(ii) Substituting 2-(3-aminopropylamino)-3-methylpyridine (2 g) for 2-(3-aminopropylamino)pyridine and using the corresponding molar proportions of the other reagents in the method of Example 1(ii) gave 2-[3-(3-methylpyrid-2-ylamino)propylamino]-5-(6-methylpyrid-3-ylmethyl)-4-pyrimidone 1.75 H$_2$O, (2.67 g; 68%) m.p. 119°–123° C. on recrystallisation from isopropanol/water.

C$_{20}$H$_{24}$N$_6$O.1.75H$_2$O: Found: C, 60.68; H, 6.71; N, 21.12; requires: C, 60.66; H, 7.00; N, 21.22%.

EXAMPLE 8

(i) Substituting 2,3-dichloropyridine (5 g) for 2-bromo-5-methylpyridine and using the corresponding molar proportions of the other reagents in the method of Example 2(i) gave 2-(3-aminopropylamino)-3-chloropyridine (4.86 g) as an oil which was used without further purification.

(ii) Substituting 2-(3-aminopropylamino)-3-chloropyridine (2.2 g) for 2-(3-aminopropylamino)pyridine and using the corresponding molar proportions of the other reagents in the method of Example 1(ii) gave 2-[3-(3-chloropyrid-2-ylamino)propylamino]-5-(6-methylpyrid-3-ylmethyl)-4-pyrimidone 1.8 H$_2$O, (3.6 g; 86%) m.p. 91°–94° C. on recrystallisation from isopropanol/water.

C$_{19}$H$_{21}$ClN$_6$O.1.8H$_2$O: Found: C, 54.8; H, 5.46; N, 20.08; Cl 8.44; requires: C, 54.68; H, 5.80; N, 20.16; Cl 8.51.

EXAMPLE 9

(i) Substituting 2,3,5-tribromopyridine (8.0 g) for 2-bromo-5-methylpyridine and using the corresponding molar proportions of the other reagents in the method of Example 2(i) gave, after stripping the final chloroform extract, an oil which was taken back up in ether, washed with dilute sodium hydroxide, dried and stripped to give 2-(3-aminopropylamino)-3,5-dibromopyridine (3.88 g) which was used without further purification.

(ii) Substituting 2-(3-aminopropylamino)-3,5-dibromopyridine (2.0 g) for 2-(3-aminopropylamino)-pyridine and using the corresponding molar proportions of the other reagents in the method of Example 1(ii) gave 2-[3-(3,5-dibromopyrid-2-ylamino)-propylamino]-5-(6-methylpyrid-3-ylmethyl)-4-pyrimidone dihydrate, (2.44 g; 81%) m.p. 160°–62° C. on recrystallisation from isopropanol/water.

$C_{19}H_{20}BrN_6O.2H_2O$: Found: C, 41.85; H, 4.42; N, 15.30; Br, 29.48%; requires: C, 41.93; H, 4.44; N, 15.44; Br, 29.37%.

EXAMPLE 10

(i) Substituting 2-bromo-3,5-dichloropyridine (7.4 g) for 2-bromo-5-methylpyridine and using the corresponding molar proportions of the other reagents in the method of Example 2(i) gave, on using ether for the final extraction, 2-(3-aminopropylamino)-3,5-dichloropyridine (4.87 g) as an oil which solidified on standing and was used without further purification.

(ii) 2-(3-Aminopropylamino)-3,5-dichloropyridine (1.0 g) and 2-nitroamino-5-(6-methylpyrid-3-ylmethyl)-4-pyrimidone (1.04 g) were fused together on an oil bath at 140° C. for 5 hr. On cooling, water was added, the pH adjusted to 7 and the resulting solid filtered off. Chromatography (silica gel, chloroform/methanol, graded elution 50:1 to 35:1) and recrystallisation from methanol afforded 2-[3-(3,5-dichloropyrid-2-ylamino)-propylamino]-5-(6-methylpyrid-3-ylmethyl)-4-pyrimidone, (0.55 g; 33%) m.p. 147°–48° C.

$C_{19}H_{20}Cl_2N_6O$: Found: C, 54.26; H, 4.59; N, 19.94; Cl, 17.19%; requires: C, 54.42; H, 4.81; N, 20.04; Cl, 16.91%.

EXAMPLE 11

(i) Substituting 2,5-dibromo-3-methylpyridine (5.0 g) for 2-bromo-5-methylpyridine and using the corresponding molar proportions of the other reagents in the method of Example 2(i) gave, on using ether in the final extraction, 2-(3-aminopropylamino)-5-bromo-3-methylpyridine (1.8 g) as an oil which was used without further purification.

(ii) Substituting 2-(3-aminopropylamino)-5-bromo-3-methylpyridine (1.76 g) for 2(3-aminopropylamino)-pyridine and using the corresponding molar proportions of the other reagents in the method of Example 1(ii) gave 2-[3-(5-bromo-3-methylpyrid-2-ylamino)-propylamino]-5-(6-methylpyrid-3-ylmethyl)-4-pyrimidone 2.1 H$_2$O, (2.44 g; 85%) m.p. 48°–51° C. on recrystallisation from isopropanol/water.

$C_{20}H_{23}BrN_6O.2.1H_2O$: Found: C, 50.17; H, 5.45; N, 17.62; Br, 16.45%; requires: C, 49.92; H, 5.70; N, 17.47; Br, 16.61%.

EXAMPLE 12

(i) Substituting 2-bromo-5-chloro-3-methylpyridine (21 g) for 2-bromo-5-methylpyridine and using the corresponding molar proportions of the other reagents in the method of Example 2(i) gave on using ether in the final extraction, 2-(3-aminopropylamino)-5-chloro-3-methylpyridine (15.5 g) as an oil which was used without further purification.

(ii) Substituting 2-(3-aminopropylamino)-5-chloro-3-methylpyridine (10 g) for 2-(3-aminopropylamino)pyridine and using the corresponding molar proportions of the other reagents in the method of Example 1(ii) gave 2-[3-(5-chloro-3-methylpyrid-2-ylamino)propylamino]-5-(6-methylpyrid-3-ylmethyl)-4-pyrimidone dihydrate, (15.25 g; 83%) m.p. 140°–43° C. on recrystallisation from isopropanol/water.

$C_{20}H_{23}ClN_6O.2H_2O$: Found: C, 55.34; H, 6.15; N, 19.38; Cl, 8.11%; requires: C, 55.23; H, 6.26; N, 19.32; Cl, 8.15%.

EXAMPLE 13

(i) 2-Chloro-3-methyl-5-nitropyridine (15.5 g), 1,3-diaminopropane (30 ml) and pyridine (10 ml) were stirred together and, after the initial exotherm had subsided, the mixture was heated under reflux for 1.5 hr. On cooling the mixture was treated with methanol and the bulk of crystalline bi-product filtered off. The solution was stripped, the residue taken up in water and the pH adjusted to 6.5 with hydrochloric acid. After filtering through 'Hyflo' the solution was extracted with chloroform. The pH was raised to 14, (NaOH) and extracted with ether. After drying (K$_2$CO$_3$), the ether extracts were stripped to give a yellow solid which was triturated with ether/pentane to give 2-(3-aminopropylamino)-3-methyl-5-nitropyridine, (12.9 g; 68%) m.p. 93°–95° C.

(ii) 2-(3-Aminopropylamino)-3-methyl-5-nitropyridine, (1.58 g) and 2-nitroamino-5-(6-methylpyrid-3-ylmethyl)-4-pyrimidone (1.44 g) were heated together under reflux in pyridine (3 ml) for 22 hr. On cooling, the mixture was treated with ethanol and a mustard coloured solid filtered off (1.88 g,) m.p. 166°–68° C. Recrystallisation from dimethyl formamide/ethanol and finally twice from dimethyl formamide/water gave 2-[3-(3-methyl-5-nitropyrid-2-ylamino)propylamino]-5-(6-methylpyrid-3-ylmethyl)-4-pyrimidone hemihydrate (1.67 g; 74%) m.p. 110° C. (softens).

$C_{20}H_{23}N_7O_3.0.5H_2O$: Found: C, 57.67; H, 5.86; N, 23.59; requires: C, 57.40; H, 5.78; N, 23.43%.

EXAMPLE 14

(i) 2-Chloro-5-fluoro-3-methylpyridine (5.4 g) 1,3-diaminopropane (15 ml) and pyridine (4 ml) were heated together under reflux for 12 hr. The mixture was stripped, the residue taken up in water and the pH adjusted to 6.5 with hydrochloric acid. After extracting with chloroform the pH was raised to 13 (NaOH) and extracted with ether. After drying (K$_2$CO$_3$) the ether extracts were stripped to give a waxy solid (3.75 g). The H$_1$-nmr spectrum of this material indicated a mixture of 3-(3-aminopropylamino)-6-chloro-5-methylpyridine and 2-(3-aminopropylamino)-5-fluoro-3-methylpyridine in the ratio 4:1.

(ii) The above mixture (2.6 g) and 2-nitroamino-5-(6-methylpyrid-3-ylmethyl)-4-pyrimidone (2.9 g) were heated together under reflux in pyridine (20 ml) for 24 hr. The mixture was stripped and the residue chromatographed (silica gel, chloroform, chloroform/methanol graded 50:1 to 20:1). Fractions containing the faster running component were combined and stripped to give a cream coloured solid (0.5 g). Recrystallisation twice from methanol and finally from methanol/water gave 2-[3-(5-fluoro-3-methylpyrid-2-yl-amino)propylamino]-5-(6-methylpyrid-3-ylmethyl)-4-pyrimidone 1.75 H$_2$O, m.p. 120°–25° C. (softens).

$C_{20}H_{23}FN_6O.1.75H_2O$: Found: C, 57.91; H, 6.17; N, 20.06; requires: C, 58.03; H, 6.45; N, 20.30%.

Fractions containing the slower running component were combined and stripped to a brown oil. This was taken up in methanol, and after treatment with charcoal, water was added to give a solid which on recrystallisation from ethanol/water afforded 2-[3-(6-chloro-5- methylpyrid-3-ylamino)propyl-amino]-5-(6-methylpyrid-3-ylmethyl)-4-pyrimidone hemihydrate (0.47 g) m.p. 110°–15° C. (softens).

$C_{20}H_{23}ClN_6O.0.5H_2O$: Found: C, 58.93; H, 5.82; N, 20.61; Cl, 8.58; requires: C, 58.89; H, 5.93; N, 20.60; Cl 8.69%.

EXAMPLE 15

(i) 2-Bromo-3,5-dimethylpyridine (12.7 g) 1,3-diaminopropane (31 ml) and pyridine (7.5 ml) were heated together under reflux for 12 hr. Working up the reaction as in the method of Example 14(i) gave 2-(3-aminopropylamino)-3,5-dimethylpyridine as an oil (2.45 g) which was used without further purification.

(ii) 2-(3-Aminopropylamino)-3,5-dimethylpyridine (0.81 g) and 2-nitroamino-5-(6-methylpyrid-3-ylmethyl)-4-pyrimidone (1.04 g) were fused together on an oil bath at 140° C. for 6 hr. On cooling the resulting mixture was equilibrated between chloroform and water (pH adjusted to 5.5 with dil. hydrochloric acid). The pH of the aqueous solution was raised to 6.5 and the product extracted out with chloroform. After drying (MgSO4) and stripping, recrystallisation from ethyl acetate and finally twice from ethanol/water gave 2-[3-(3,5-dimethylpyrid-2-ylamino)propylamino]-5-(6-methylpyrid-3-ylmethyl)-4-pyrimidone 2.4H2O, (0.83 g; 49%) m.p. 104°–5° C. (softens ca 90° C.).

$C_{21}H_{26}ClN_6O.2.4H_2O$: Found: C, 59.59; H, 7.07; N, 19.96; requires: C, 59.81; H, 7.36; N, 19.93%.

EXAMPLE 16

2-(3-Aminopropylamino)pyridine (0.91 g) and 5-(4-chlorobenzyl)-2-methylthio-4-pyrimidone (1.33 g) were fused together on a oil bath at 160° C. for 2.5 hr. The mixture was dissolved in hot ethanol. Cooling afforded a white solid which on recrystallisation from ethanol gave 5-(4-chlorobenzyl)-2-[3-(pyrid-2-ylamino)propylamino]-4-pyrimidone, (1.24 g; 67%) m.p. 168°–71° C.

$C_{19}H_{20}ClN_5O$: Found: C, 61.41; H, 5.42; N, 18.83; requires: C, 61.70; H, 5.45; N, 18.94%.

EXAMPLE 17

2-(3-Aminopropylamino)-3-chloropyridine (1 g) and 5-(4-chlorobenzyl)-2-methylthio-4-pyrimidone (1.3 g) were heated together under reflux in pyridine (20 ml) for 48 hr. The mixture was stripped and recrystallised from dimethyl formamide/ethanol/water to give 5-(4-chlorobenzyl)-2-[3-(3-chloropyrid-2-ylamino)propylamino]-4-pyrimidone 0.7H2O, (1.55 g; 76%) m.p. 180°–81° C.

$C_{19}H_{19}ClN_5O.0.7H_2O$: Found: C, 54.87; H, 5.02; N, 17.01; Cl, 17.09; requires: C, 54.74; H, 4.93; N, 16.80; Cl, 17.01%.

EXAMPLE 18

2-(3-Aminopropylamino)-5-chloro-3-methylpyridine (0.92 g) and 2-methylthio-5-(4-pyridylmethyl)-4-pyrimidone (0.90 g) were heated together under reflux in pyridine (5 ml) for 46 hr. After stripping to dryness the residue was triturated with wet ether to give a white solid. Repeated recrystallisation from isopropanol/water gave 2-[3-(5-chloro-3-methylpyrid-2-ylamino)propylamino]-5-(4-pyridylmethyl)-4-pyrimidone (0.95 g; 64%) m.p. 90°–92° C.

$C_{19}H_{21}ClN_6O$: Found: C, 58.87; H, 5.20; N, 21.58; Cl, 8.84; requires: C, 59.29; H, 5.50; N, 21.84; Cl, 9.21%.

EXAMPLE 19

(i) Substituting 1,4-diaminobutane (440 g) for 1,3-diaminopropane and using the corresponding molar proportions of the other reagents in the method of Example 1(i) and heating under reflux for 4 hr gave, after distillation, 2-(4-aminobutylamino)pyridine, (131.1 g; 79%) b.p.$_{0.3}$ 128°–30° C.

(ii) Substituting 2-(4-aminobutylamino)pyridine (1.8 g) for 2-(3-aminopropylamino)pyridine and using the corresponding molar proportions of the other reagents in the method of Example 1(ii) gave 2-[4-(pyrid-2-ylamino)butylamino]-5-(6-methylpyrid-3-ylmethyl)-4-pyrimidone, (2.78 g; 76%) m.p. 184° C. on recrystallisation from ethanol.

$C_{20}H_{24}N_6O$: Found: C, 65.54; H, 6.51; N, 23.21; requires: C, 65.89; H, 6.64; N, 23.07%.

EXAMPLE 20

(i) Substituting 1,2-diaminoethane (10.16 g) for 1,3-diaminopropane and using the corresponding molar proportions of the other reagents in the method of Example 3(i) gave, on using ether for the final extraction, 2-(2-aminoethylamino)-5-chloropyridine (3.57 g) as an oil which was used without further purification.

(ii) Substituting 2-(2-aminoethylamino)-5-chloropyridine (2.0 g) for 2-(3-aminopropylamino)pyridine and using the corresponding molar proportions of the other reagents in the method of Example 1(ii) gave 2-[2-(5-chloropyrid-2-ylamino)ethylamino]-5-(6-methylpyrid-3-ylmethyl)-4-pyrimidone hemihydrate, (2.95 g; 75%) m.p. 164°–66° C. on recrystallisation from isopropanol/water.

$C_{18}H_{19}ClN_6O.0.5H_2O$: Found: C, 57.25; H, 5.31; N, 22.18; Cl, 9.18; requires: C, 56.92; H, 5.31; N, 22.13; Cl, 9.33%.

EXAMPLE 21

(i) Substituting 1,4-diaminobutane (15.8 g) for 1,3-diaminopropane and using the corresponding molar proportions of the other reagents in the method of Example 3(i) gave, on using ether in the final extraction, 2-(4-aminobutylamino)-5-chloropyridine (6.53 g) as an oil which was used without further purification.

(ii) Substituting 2-(4-aminobutylamino)-5-chloropyridine (2 g) for 2-(3-aminopropylamino)pyridine and using the corresponding molar proportions of the other reagents in the method of Example 1(i) gave 2-[4-(5-chloropyrid-2-ylamino)butylamino]-5-(6-methylpyrid-3-ylmethyl)-4-pyrimidone, (2.34 g; 76%) m.p. 214°–15° C. on recrystallisation from dimethyl formamide/ethanol.

$C_{20}H_{23}ClN_6O$: Found: C, 59.81; H, 5.69; N, 20.71; Cl, 8.51; requires: C, 60.2; H, 5.82; N, 21.08; Cl, 8.89.

EXAMPLE 22

(i) Substituting 1,4-diaminobutane (15.8 g) for 1,3-diaminopropane and using the corresponding molar proportions of the other reagents in the method of Example 8(i) gave, on using ether for the final extraction 2-(4-aminobutylamino)-3-chloropyridine (4.44 g) as an oil which was used without further purification.

(ii) Substituting 2-(4-aminobutylamino)-3-chloropyridine (1.8 g) for 2-(3-aminopropylamino)pyridine and using the corresponding molar proportions of the other reagents in the method of Example 1(ii) gave 2-[4-(3-chloropyrid-2-ylamino)butylamino]-5-(6-methylpyrid- 3-ylmethyl)-4-pyrimidone (2.35 g; 78%) m.p. 180°–82° C. on recrystallisation from ethanol.

$C_{20}H_{23}ClN_6O$: Found: C, 60.22; H, 5.70; N, 21.07; Cl, 8.64; requires: C, 60.20; H, 5.82; N, 21.08; Cl, 8.89%.

EXAMPLE 23

(i) Substituting 1,2-diaminoethane (9.0 g) for 1,3-diaminopropane and using the corresponding molar proportions of the other reagents in the method of Example 12(i) gave 2-(2-aminoethylamino)-5-chloro-3-methylpyridine (3.37 g) as an oil which was used without further purification.

(ii) Substituting 2-(2-aminoethylamino)-5-chloro-3-methylpyridine (3.35 g) for 2-(3-aminopropylamino)-pyridine and using the corresponding molar proportions of the other reagents in the method of Example 1(ii) gave 2-[2-(5-chloro-3-methylpyrid-2-ylamino)ethylamino]-5-(6-methylpyrid-3-ylmethyl)-4-pyrimidone 1.45H$_2$O, (5.28 g; 86%) m.p. 112°–15° C. on recrystallisation from isopropanol/water.

$C_{19}H_{21}ClN_6O.1.45H_2O$: Found: C, 55.81; H, 5.60; N, 20.35; Cl, 8.49; requires: C, 55.53; H, 5.80; N, 20.47; Cl, 8.64%.

EXAMPLE 24

(i) Substituting 1,4-diaminobutane (13.2 g) for 1,3-diaminopropane and using the corresponding molar proportions of the other reagents in the method of Example 12(i) gave 2-(4-aminobutylamino)-5-chloro-3-methylpyridine (3.8 g) as an oil which was used without further purification.

(ii) 2-(4-Aminobutylamino)-5-chloro-3-methylpyridine (1.81 g) and 2-nitroamino-5-(6-methylpyrid-3ylmethyl)-4-pyrimidone (1.95 g) were fused together on an oil bath at 140°–50° C. for 2 hr. On cooling the mixture was treated with water and dilute hydrochloric acid and some solid material removed at pH 4. On raising the pH to 5 a precipitate was obtained which on recrystallising twice from dimethyl formamide/water gave 2-[4-(5-chloro-3-methylpyrid-2-ylamino)butylamino]-5-(6-methylpyrid-3-ylmethyl)-4-pyrimidone (1.2 g; 39%) m.p. 202°–3° C.

$C_{21}H_{25}ClN_6O$: Found: C, 61.18; H, 5.91; N, 20.38; Cl, 8.29; requires: C, 61.08; H, 6.10; N, 20.35; Cl, 8.59%.

EXAMPLE 25

(i) 2-(Aminopropylamino)-5-chloro-3-methylpyridine (3.17 g) and 2-nitroamino-5-(N-oxo-6-methylpyrid-3-ylmethyl)-4-pyrimidone (3.67 g) were heated together under reflux in pyridine (30 ml) for 7 hr. The mixture was stripped and the residue recrystallised twice from isopropanol/water to give 2-[3-(5-chloro-3-methylpyrid-2-ylamino)propylamino]-5-(N-oxo-6-methylpyrid-3-ylmethyl)-4-pyrimidone (3.51 g; 66%) m.p. 128°–31° C.

(ii) Trifluoroacetic anhydride (9 ml) was added to a stirred suspension of 2-[3-(5-chloro-3-methylpyrid-2-ylaminopropylamino]-5-(N-oxo-6-methylpyrid-3-ylmethyl)-4-pyrimidone (3.45 g) in dry dichloromethane (70 ml) at room temperature. On solution the mixture was set aside for 6 days. After this time the mixture was stripped to dryness and then stripped to dryness twice from methanol. The residue was taken up in water and extracted with chloroform. The pH of the aqueous solution was raised to 4.5 and extracted again with chloroform. The pH was finally adjusted to 6.5 to yield a precipitate which was recrystallised from dimethyl formamide/ethanol to give 2-[3-(5-chloro-3-methylpyrid-2-ylamino)propylamino]-5-(6-hydroxymethylpyrid-3-ylmethyl)-4-pyrimidone monohydrate, (0.58 g; 17%) m.p. 207°–209° C.

$C_{20}H_{23}ClN_6O.1H_2O$: Found: C, 57.92; H, 5.85; N, 20.26; Cl, 8.34; requires: C, 57.62; H, 6.04; N, 20.16; Cl, 8.50%.

EXAMPLE 26

(i) 2-(3-Aminopropylamino)-3,5-dichloropyridine (1.43 g) and 2-nitroamino-5-(N-oxo-6-methylpyrid-3-ylmethyl)-4-pyrimidone(1.52 g) were heated together under reflux in pyridine (15 ml) for 7 hr. The solution was stripped and the residue boiled with chloroform. On cooling, the solid obtained was recrystallised from dimethyl formamide to give 2-[3-(3,5-dichloropyrid-2-ylamino)propylamino]-5-(N-oxo-6-methylpyrid-3-ylmethyl)-4-pyrimidone, (1.5 g; 63%) m.p. 208°–210° C.

(ii) Substituting 2-[3-(3,5-dichloropyrid-2-ylamino)propylamino]-5-(N-oxo-6-methylpyrid-3-ylmethyl)-4-pyrimidone (1.45 g) for 2-[3-(5-chloro-3-methylpyrid-2-ylamino)propylamino]-5-(N-oxo-6-methylpyrid-3-ylmethyl)-4-pyrimidone and using corresponding molar proportions of the other reagents in the method of Example 25(ii) gave, after chromatography (silica gel chloroform/methanol graded 50:1 to 20:1) and repeated recrystallisation from dimethyl formamide/ethanol and finally dimethyl formamide/ethanol/water 2-[3-(3,5-dichloropyrid-2-ylamino)propylamino]-5-(6-hydroxymethylpyrid-3-ylmethyl)-4-pyrimidone, (0.2 g; 14%) m.p. 184°–186° C.

$C_{19}H_{20}Cl_2N_6O_2$+1% NaCl: Found: C, 51.80; H, 4.70; N, 19.06; Cl, 16.56; requires: C, 51.90; H, 4.59; N, 19.11; Cl, 16.73%.

EXAMPLE 27

(i) Substituting 2-bromo-4-methylpyridine (25.8 g) for 2-bromo-5-methylpyridine and using the corresponding molar proportions of the other reagents in the method of Example 2(i) gave 2-(3-aminopropylamino)-4-methylpyridine, (16.1 g; 65%) b.p.$_{0.01-0.02}$120°–124° C.

(ii) Substituting 2-(3-aminopropylamino)-4-methylpyridine (1.0 g) for 2-(3-aminopropylamino)pyridine and using the corresponding molar proportions of the other reagents in the method of Example 1(ii) gave 2-[3-(4-methylpyrid-2-ylamino)propylamino]-5-(6-methylpyrid-3-ylmethyl)-4-pyrimidone 0.3 H$_2$O, (1.41 g; 77%) m.p. indeterminate, on the recrystallisation from ethanol/water.

$C_{20}H_{24}N_6O.0.3H_2O$: Found: C, 64.75; H, 6.67; N, 22.93; requires: C, 64.95; H, 6.70; N, 22.72.

EXAMPLE 28

(i) Substituting 2-bromo-6-methylpyridine (25.8 g) for 2-bromo-5-methylpyridine and using the corresponding molar proportions of the other reagents in the method of Example 2(i) gave 2-(3-aminopropylamino)-6-methylpyridine, (11.11 g; 45%) b.p.$_{0.4}$121°–123° C.

(ii) Substituting 2-(3-aminopropylamino)-6-methylpyridine (1.0 g) for 2-(3-aminopropylamino)pyridine and using the corresponding molar proportions of the other reagents in the method of Example 1(ii) gave 2-[3-(6-methylpyrid-2-ylamino)propylamino]-5-(6-methylpyrid-3-ylmethyl)-4-pyrimidone 0.5 H$_2$O, (1.21 g; 65%) m.p. ca. 113°–120 ° C. on recrystallisation from ethanol/water.

$C_{20}H_{24}N_6O.0.5H_2O$: Found: C, 64.30; H, 6.55; N, 22.75; requires: C, 64.32; H, 6.46; N, 22.50%.

What is claimed is:

1. A compound of the formula:

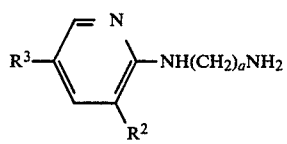
where
R[2] is $C_{1-4}$ alkyl, $C_{1-4}$ alkoxy, halogen, nitro, cyano or trifluoromethyl;
R[3] is halogen; and
a is 2 to 4.
2. A compound according to claim 1 where $R_3$ is chlorine.
* * * * *